United States Patent
Sumner

(10) Patent No.: US 7,892,414 B1
(45) Date of Patent: Feb. 22, 2011

(54) ELECTROCHEMICAL BIOSENSORS, APPLICATIONS AND METHODS OF MAKING BIOSENSORS

(75) Inventor: James J. Sumner, Columbia, MD (US)

(73) Assignee: The United States of America as represented by the Secretary of Army, Washington, DC (US)

( * ) Notice: Subject to any disclaimer, the term of this patent is extended or adjusted under 35 U.S.C. 154(b) by 1211 days.

(21) Appl. No.: 11/274,709

(22) Filed: Nov. 15, 2005

Related U.S. Application Data

(60) Provisional application No. 60/634,509, filed on Nov. 19, 2004.

(51) Int. Cl.
*G01N 27/327* (2006.01)
*G01N 27/26* (2006.01)

(52) U.S. Cl. ............ 205/778; 204/403.01; 422/82.02; 436/806

(58) Field of Classification Search ............ 204/403, 204/400, 403.01; 205/198, 778, 777.5; 435/14; 422/68.1, 82.02; 436/806
See application file for complete search history.

(56) References Cited

U.S. PATENT DOCUMENTS

| | | | |
|---|---|---|---|
| 4,286,087 A | 8/1981 | Austin | |
| 4,895,724 A | 1/1990 | Cardinal | |
| 5,015,293 A | 5/1991 | Mayer | |
| 5,328,847 A * | 7/1994 | Case et al. | 205/778 |
| 5,494,831 A * | 2/1996 | Kindler | 205/777.5 |
| 5,525,710 A | 6/1996 | Unger | |
| 5,540,828 A * | 7/1996 | Yacynych | 205/198 |
| 5,589,396 A | 12/1996 | Frye | |
| 5,620,706 A | 4/1997 | Dumitriu | |
| 5,624,537 A | 4/1997 | Turner | |
| 5,830,883 A | 11/1998 | Block | |
| 5,840,341 A | 11/1998 | Watts | |
| 5,871,985 A | 2/1999 | Aebischer | |
| 5,919,576 A * | 7/1999 | Hui et al. | 428/545 |
| 6,165,335 A * | 12/2000 | Lennox et al. | 204/403.01 |

(Continued)

OTHER PUBLICATIONS

Julia M.C.S. Magalhaes, Adelio A.S.C Machado, Urea Potentiometric Biosensor Based on Urease Immobilized on Chitosan Membranes, Feb. 11, 1998, Elsevier Science B.V., 47, 183-184.*

(Continued)

*Primary Examiner*—Alexa D Neckel
*Assistant Examiner*—Jennifer Dieterle
(74) *Attorney, Agent, or Firm*—William W. Randolph; Lawrence E. Anderson

(57) ABSTRACT

Electrochemical biosensors, methods of making biosensors and methods of detecting a target analyte in a sample to be analyzed are provided. A preferred embodiment device comprises a non-conductive polymer deposited on the electrode to form a matrix material having a plurality of pores; a capture biomolecule immobilized on the electrode such that the binding of the target analyte to the capture biomolecule effectively blocks a sufficient number of pores in the matrix material to produce a measurable decrease in the rate of a redox reaction occurring at the electrode; a current source for driving a redox reaction at the electrode; a redox species in contact with the electrode; and a detector element operatively connected to the electrode to detect the measureable decrease of a change in the rate of a redox reaction occurring due to the blockage of pores in the matrix material by the target analyte.

21 Claims, 8 Drawing Sheets

U.S. PATENT DOCUMENTS

| | | | |
|---|---|---|---|
| 6,268,161 B1 * | 7/2001 | Han et al. | 435/14 |
| 6,332,363 B1 | 12/2001 | Molloy | |
| 6,485,987 B1 | 11/2002 | Charych | |
| 6,551,496 B1 | 4/2003 | Moles | |
| 6,773,723 B1 | 8/2004 | Spiro | |
| 6,800,448 B2 | 10/2004 | Rider | |
| 6,960,466 B2 | 11/2005 | Pamidi | |

OTHER PUBLICATIONS

Xu et al., Electrochemical detection of sequence-specific DNA using a DNA probe labeled with aminoferrocene and chitosan modified electrode immobilized with ssDNA, Royal Society of Chemistry, Dec. 18, 2000, p. 1-9.*

Wu et al., Voltage-Dependent Assembly of the Polysaccharide Chitosan onto an Electrode Surface, American Chemical Society, Sep. 21, 2002, pp. 8620-8625.*

Fernandes et al., Electrochemically Induced Deposition of a Polysaccharide Hydrogel onto a Patterned Surface, American Chemical Society, Apr. 15, 2003, pp. 4058-4062.*

Yang et al. (Amperometric glucose biosensor based on chitosan with improved selectivity and stability, Elsevier, May 25, 2004, pp. 269-276.*

Magalhaes et al., Urea Potentiometric Biosensor Based on Urease Immobilized on Chitosan Membranes, Talanta 47, 1998, pp. 183-191.*

Ye et al., High-density, microsphere-based fiber optic DNA microarrays, MDPI, Jun. 28, 2003, pp. 128-145.*

DeLisa J et al. "DNA Microarray-Based Identification of Genes Controlled by Autoinducer 2-Stimulated Quorum Sensing in *Escherichia*," Journal of Bacteriology, Sep. 2001, p. 5239-5247.

Dari Shalon, Stephen J. Smith, and Patrick O. Brown, "A DNA Microarray System for Analyzing Complex DNA Samples Using Two-color Fluorescent Probe Hybridization," Genome Res. 1996,7,639-645.

Sumner, J.J. and S.E. Creager, Redox kinetics in monolayers on electrodes: Electron transfer is sluggish for ferrocene groups buried within the monolayer interior. Journal of Physical Chemistry B, 2001. 105(37): p. 8739-8745.

C. J. Yu,, Yanjian Wan, Handy Yowanto, Jie Li, Chunlin Tao, Matthew D. James, Christine L. Tan, Gary F. Blackburn, and Thomas J. Meade "Electronic Detection of Single-Base Mismatches in DNA with Ferrocene-Modified Probes," J. Am. Chem. Soc. 2001, 123, 11155-11161.

Wang, I.; Liu, G.D.; Merkoci, A. Particle-based detection of DNA hybridization . . . stripping measurements of an iron tracer, Anal. Chim. Acta 2003, 482, 149-155.

J. Wang, A. N. Kawde, and M. Musameh, "Carbon-nanotube-modified glassy carbon electrodes for amplified label-free electrochemical detection of DNA hybridization," M. Analyst 2003,128,912-916.

Armistead, P.M.; Thorp, H.H. "Modification of Indium Tin Oxide Electrodes with Nucleic Acids: Detection of Attomole Quantities of Immobilized DNA by Electrocatalysis,"Anal. Chem. 2000,72,3764-3770.

Fernandes, R.; Wu, L.Q.; Chen, T.; Yi, H. ; Rubloff, G.W.; Ghodssi, R.; Bentley, W.E.; Payne, G.F., "Electrochemically Induced Deposition of a Polysaccharide Hydrogel onto a Patterned Surface," Langmuir 2003, 19,4058-4062.

Wu, L.Q.; Gadre, A.P.; Yi, H.; Kastantin, M.1.; Rubloff, G.W.; Bentley, W.E.; Payne, G.F.; Ghodssi, R., "Voltage-Dependent Assembly of the Polysaccharide Chitosan onto an Electrode Surface," Langmuir 2002,18,8620-8625.

Yi, H.; Wu, L.Q.; Sumner, I.J.; Gillespie, J.B.; Payne, G.F.; Bentley, W.E., "Chitosan scaffolds for biomolecular assembly: Coupling nucleic acid probes for detecting hybridization," Biotechnology and Bioengineering 2003, 83, 646-652.

Tianhong Chen, Rafael Vazquez-Duhalt, Chi-Fang Wu ,| William E. Bentley,| and Gregory F. Payne "Combinatorial Screening for Enzyme-Mediated Coupling. Tyrosinase-Catalyzed Coupling to Create Protein-Chitosan Conjugates," Biomacromolecules 2001, 2, 456-462.

Li-Qun Wu, Hyunmin Yi, Sheng Li, Gary W. Rubloff, William E. Bentley, Reza Ghodssi, and Gregory F. Payne, "Spatially Selective Deposition of a Reactive Polysaccharide Layer onto a Patterned Template," Langmuir 2003, 19, 519-524.

Tianhong Chen, David A. Small, Li-Qun Wu, Gary W. Rubloff, Reza Ghodssi, Rafael Vazquez-Duhalt, William E. Bentley, and Gregory F. Payne "Nature-Inspired Creation of Protein-Polysaccharide Conjugate and Its Subsequent Assembly onto a Patterned Surface," Langmuir, 2003, 19 (22), 9382-9386.

* cited by examiner

ELECTROCHEMICAL BIOSENSORS, APPLICATIONS AND METHODS OF MAKING BIOSENSORS

CROSS-REFERENCE TO RELATED APPLICATION

This application claims priority to U.S. provisional application entitled, "An Electrochemical Biosensor Based on Molecular-Scale Gates," having Ser. No. 60/634,509, filed Nov. 19, 2004, which is entirely incorporated herein by reference.

FIELD OF THE INVENTION(S)

The present disclosure is generally related to electrochemical biosensors, methods of making biosensors and methods of detecting a target analyte in a sample to be analyzed.

BACKGROUND

In general, a biosensor is a device capable of identifying a target biomolecule such as a polynucleotide, polypeptide, or other biomolecule of interest. There is great interest in developing biosensors to be used for varied purposes from monitoring gene expression in organisms to identification and speciation of possible pathogens and/or biocontaminants to the identification of drug candidates. Such devices would be a great benefit for food and water safety monitoring, medical diagnostics, and defense of military and civilian populations from biological threats. Sensors developed for the detection of biological analytes are typically based on ligand specific binding events between a recognition binding pair, such as antigen-antibody, hormone-receptor, drug-receptor, cell surface antigen-lectin, biotin-avidin, and complementary nucleic acid strands. The analyte to be detected may be either member of the binding pair, or the target analyte may be a ligand analog that competes with the ligand for binding to the complement receptor.

Traditional biosensors designed for the purpose of detecting binding events between complementary binding pairs, such as those described above, are large, and require significant volumes of liquid reagents and highly trained personnel. Typically, the reduction or elimination of any of these requirements leads to a subsequent loss of sensitivity and/or selectivity. Over the past several years researchers have been striving to develop alternatives to current biosensor technologies, but many developments have been geared to large, array-based equipment to increase sensitivity or throughput in the laboratory setting.

Examples of some of these efforts include optical biosensors that employ recognition elements to detect a target analyte, such as nucleic acid (e.g., DNA or RNA) hybridization assays. Such hybridization assays have been developed to interrogate samples for multiple analytes from a single sample. Nucleic acid based biosensors can be very selective; however, the optical techniques employed in many such sensors require multiple liquid reagents which must be stored in controlled environments and fluorescent labels that can be unstable. Labeling of biological molecules can be very expensive and produce low yields. Also the need for optics to excite or collect fluorescent signal adds expensive and complicated components and creates alignment issues. It would be desirable to reduce the reagent load, remove the fluorescent labels, reduce manufacturing and operational costs and make the sensing element reusable.

Biosensors incorporating electrochemical techniques were developed in order to meet some of these needs. A typical electrochemical biosensor includes a base electrode and a biochemically discriminating element in contact or otherwise coupled to the electrode. The biochemically discriminating element functions either to detect and transform the target analyte into an electrically active species, which is then detected by the electrode, or to otherwise generate an electrical signal, which is sensed and monitored by the electrode.

The application of electrochemical techniques to biosensor technology holds many advantages over optical techniques including, but not limited to, the lack of optical elements to align, the ability to operate in turbid media such as blood or waste water, as well as the ability to capitalize on the vast electronics processing industry for electrode arrays and control electronics. However, manufacture and use of such electrochemical biosensors has proven challenging due to complicated designs and electrochemical interferences caused by interactions of substances other than the target analyte.

Due to the difficulty of converting a biochemical binding event into an electrochemical signal, early applications of electrochemical biosensors were designed for detecting analytes that are themselves electrochemical species, or that can participate in reactions that generate electrochemical species, rather than to direct detection of ligand-receptor binding events. However, such sensors are quite limited in their application. In an effort to overcome this problem, sensors were developed that involve an intermediate reaction or a secondary active species of some sort, which acts to generate the electrochemical signal. One such design includes two separate reaction elements in the biosensor: a first element contains a receptor and bound enzyme-linked ligand, and the second element includes components for enzymatically generating and then measuring an electrochemical species. In operation, analyte ligand displaces the ligand-enzyme conjugate from the first element, releasing the enzyme into the second element region, thus generating an electrochemical species which is measured in the second element. Two-element biosensors of this type are relatively complicated to produce, thus limiting their usefulness.

Biosensors that attempt to couple electrochemical activity directly to a ligand-receptor binding event without the use of two reaction elements have been proposed where a lipid bi-layer membrane containing an ion-channel receptor that is either opened or closed by ligand binding to the receptor controls access to the electrode. Electrodes of this type are also complicated, difficult to make and store, and are limited at present to a rather small group of receptor proteins.

As discussed, many of the above techniques have disadvantages such as complicated design, expensive reagents and manufacturing costs, use of fluorescent tags, applicability to only a small class of biomolecules, and complicated, multi-step processing. Thus, there is a need in the industry for a biosensor that overcomes at least these disadvantages, such as a biosensor utilizing porous materials attached to electrodes.

Examples of biosensor applications include U.S. Pat. Nos. 5,589,396 (Frye, et. al.), 5,624,537 (Turner, et. al.), 6,332,363 (Molloy, et. al.), 6,485,987 (Charych, et al.), 6,551,496 (Moles, et. al.), 6,800,448 (Rider et. al.), 6,960,466 (Pamidi, et. al.), and examples of porous materials include U.S. Pat. Nos. 4,286,087 (Austin, et. al.), 4,895,724 (Cardinal, et. al.), 5,015,293 (Mayer, et. al.), 5,525,710 (Unger, et. al.), 5,620,706 (Dumitriu, et. al.), 5,830,883 (Block, et. al.), 5,840,341 (Watts, et. al.), 5,871,985 (Aebischer, et. al.), and 6,773,723 (Spiro et. al.), the teachings all of the above U.S. Patents are fully incorporated by reference.

SUMMARY

Embodiments of the present disclosure provide novel biosensors, methods of making the biosensors and methods of detecting a target analyte. Briefly described, one embodiment of the biosensor of the present invention, among others, includes: an electrode, a matrix material deposited on the electrode with pores throughout the matrix material to create pathways for redox molecules to reach the electrode, and a capture biomolecule immobilized on the matrix material. When the capture biomolecule binds a target analyte, the bound analyte blocks a number of the pathways defined by the pores in the matrix material to sufficiently inhibit the passage of redox molecules to result in a measurable decrease in the rate of a redox reaction occurring at the electrode. Embodiments of the sensor further include a current source to drive a redox reaction at the electrode and a signal element to detect and report a change in the rate of the redox reaction occurring at the electrode. While in some embodiments of the biosensor the capture biomolecule binds directly to the matrix material, other embodiments further include a linking material to immobilize the capture biomolecule to the matrix material.

Embodiments of the present disclosure also include methods for making a biosensor. One embodiment of such a method, among others, can be broadly summarized by the following steps: providing an electrode, electrochemically depositing a porous matrix material on the surface of the electrode, immobilizing a capture biomolecule capable of binding a target analyte onto the matrix material, and coupling the electrode to a signal element to detect and report a change in the rate of a redox reaction occurring at the electrode.

Embodiments of the present disclosure further include methods for detecting a biomolecule of interest (i.e., a target analyte). One embodiment, among others, of such a method generally includes the following steps: immersing an electrode, which is substantially coated with a porous matrix material and has capture biomolecules immobilized to the matrix material, into a sample to be analyzed; providing a flow of electrons to drive a redox reaction at the electrode; and detecting and reporting a change in the rate of a redox reaction occurring at the electrode, which signals the binding of the target analyte to the capture biomolecule.

Other systems, methods, features and/or advantages of the present disclosure will be, or become apparent to one with skill in the art upon examination of the following drawings and detailed description. It is intended that all such additional systems, methods, features and/or and advantages be included within this description and be protected by the accompanying claims.

BRIEF DESCRIPTION OF THE FIGURES

Aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Embodiments of the present invention provide inexpensive, simple and compact biosensors, methods of making such biosensors and methods of using the biosensors to detect a target analyte. There is a great need for this type of technology for applications including, but not limited to, military and civilian security, environmental safety, medical diagnostics, genetic mapping, and drug discovery. The biosensors of the present invention provide many advantages, including, but not limited to, the low cost of manufacture, relatively easy assembly out of inexpensive and stable reagents, low operating costs due to low power platform, the ability to manufacture the sensor in small sizes, and the adaptability to producing the sensors in an array format for high-throughput applications.

The biosensors of the present disclosure employ an electrochemical approach, utilizing an electrode which is controlled by "molecular-scale gates" capable of being activated by a biological agent. The gates are formed by a matrix material deposited on the electrode in such a manner that pores in the matrix material provide pathways to allow a redox species (e.g., redox molecules contained in an aqueous electrolyte solution) to reach the electrode for reaction. A recognition binding pair made up of a capture biomolecule and a target analyte serve as "switches", which, when unhybridized or unbound, will leave these pathways open. These "switches" will close upon the binding of one half of the recognition binding pair, the target analyte contained in the sample, to the other half of the binding pair, the capture biomolecule immobilized on the matrix material. The system is interrogated by standard electrochemical techniques to detect binding of the target analyte. When bound, the switches close the gates thereby blocking the passage of the redox species to the electrode and reducing the rate of a redox reaction occurring at the electrode, which can be detected by a signal element.

Figure 1:
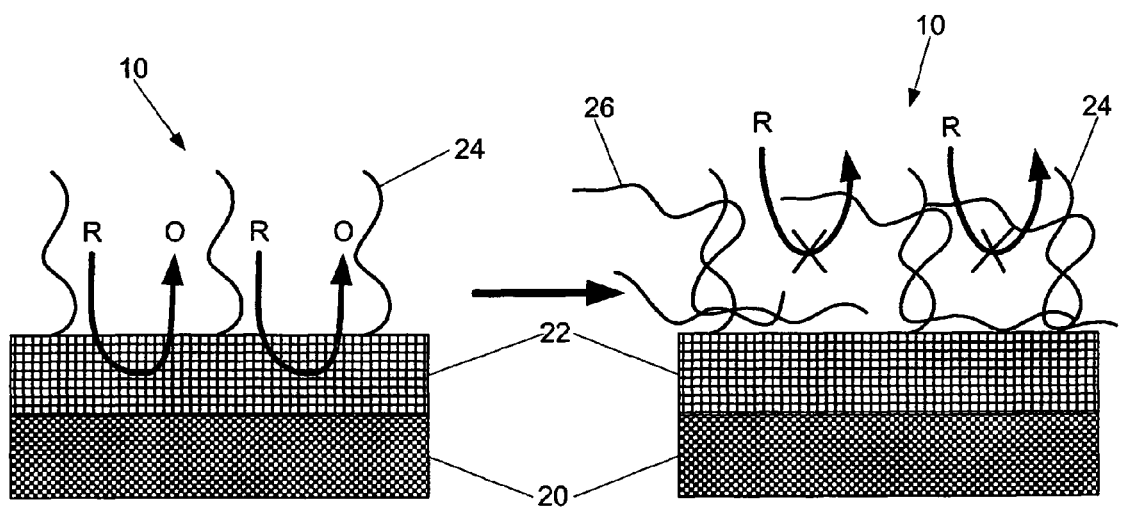
FIG. 1 is a simplified diagram of one embodiment of the working electrode of the biosensor of the present disclosure, illustrating the operation of the biosensor before and after binding of a target analyte.

FIG. 1 generally illustrates the biosensor of the present disclosure, with a working electrode 10, having an electrode 20 and matrix material 22. A capture biomolecule 24 is bound to the matrix material. In the open-gate configuration, a redox reaction occurs by the passage of a redox species through the pores in the matrix material to the electrode. In the closed-gate configuration, a capture biomolecule 26 hybridizes to the capture biomolecule 24 and blocks the passage of the redox species, thereby preventing, or at least reducing, the rate of a redox reaction at the electrode, which is measured using standard electrochemical techniques known to those of skill in the art and discussed in greater detail below.

The electrode may be made of any conductive material generally used for electrodes. Possible materials include carbon, platinum, and various coinage metals, including, but not limited to gold, silver, and copper. In a preferred embodiment, the electrode is gold.

The matrix material may be any non-conductive material that can be deposited on an electrode in such a manner as to provide a porous barrier between the electrode and its surrounding environment. The material is preferably of sufficient thickness to at least partially inhibit the flow of a redox species to the electrode, but the pores are of a sufficient diameter to create a pathway for the flow of a redox species to the electrode. The appropriate thickness of the matrix material depends, in part, on the specific application of the biosensor. In some embodiments of the biosensor the matrix material is between about 1 micron and about 100 microns thick, more preferably between about 1 micron and about 10 microns thick. Preferably the matrix material also has a binding functionality to allow for the immobilization of a capture biomolecule, either directly or through the use of a linking material. Possible binding functionalitys include, but are not limited to, amide, imine, ester, ether, and sulfhydryl linkages.

Figure 2:
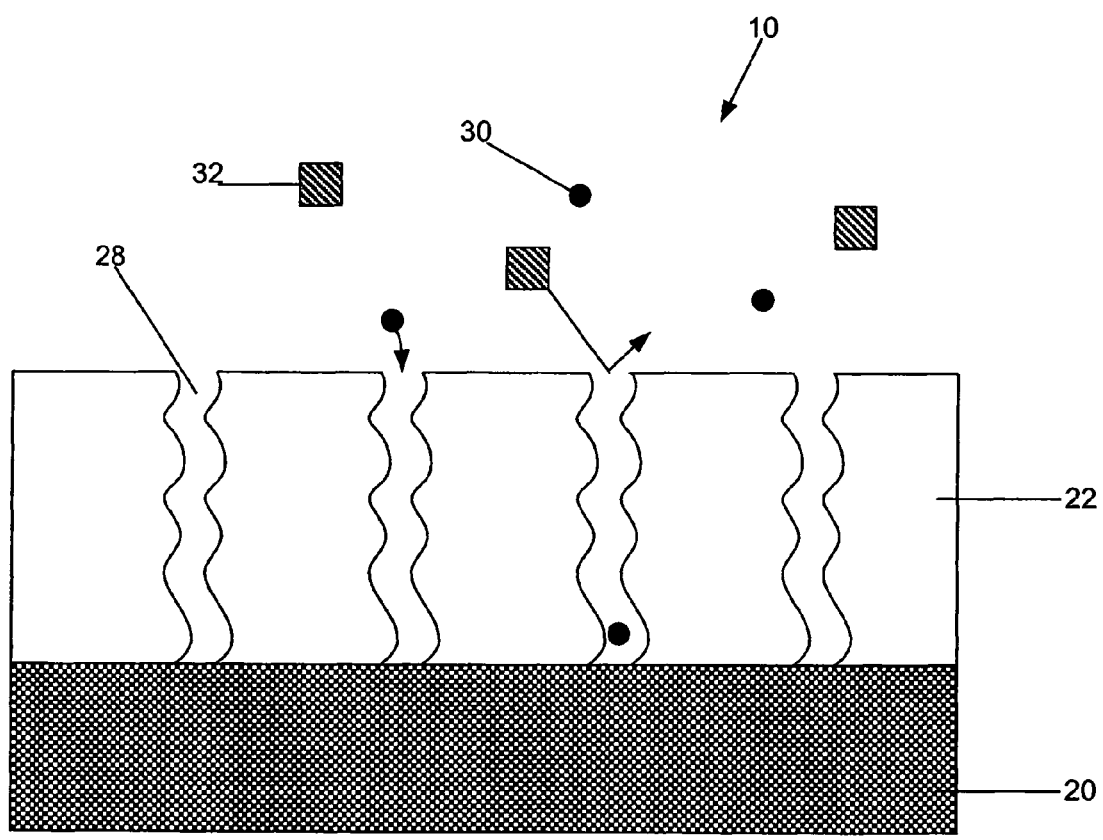
FIG. 2 is a simplified illustration of an enlarged view of a region of the working electrode of a biosensor according to the present disclosure on which matrix material has been deposited.

FIG. 2 depicts an enlarged view of a portion a working electrode 10 of an embodiment of the biosensor according to the present disclosure, including an electrode 20 covered with a matrix material 22. In the embodiment shown, the matrix material 22 has pores 28 that are of a sufficient diameter to permit the flow of redox molecules 30 through the matrix to the electrode for a redox reaction, but exclude the passage of larger, potentially contaminating molecules 32 that may be present in the sample to be analyzed. This inhibits the reaction of such molecules with the electrode and thus significantly reduces interference with the biosensor operation often caused by common contaminants.

In preferred embodiments, the matrix material is a non-conductive polymer material having a binding functionality for binding either a capture biomolecule or a linking material. Even more preferably, the matrix material is also substantially soluble at a generally high or generally low pH and substantially insoluble at a generally neutral pH, which is usually the working pH of the biosensor. This is advantageous for at least two reasons: 1) the relative solubility of the matrix material at a high or low pH facilitates the preparation of the electrode by performing the deposition of the matrix material onto the electrode at a low or high pH, as appropriate, as illustrated in the examples below, and 2) the relative insolubility of the matrix material at a generally neutral pH provides that the matrix material will not likely go into solution at the working pH, which could disrupt the matrix pathways and interfere with the biosensor functions.

Figure 3:
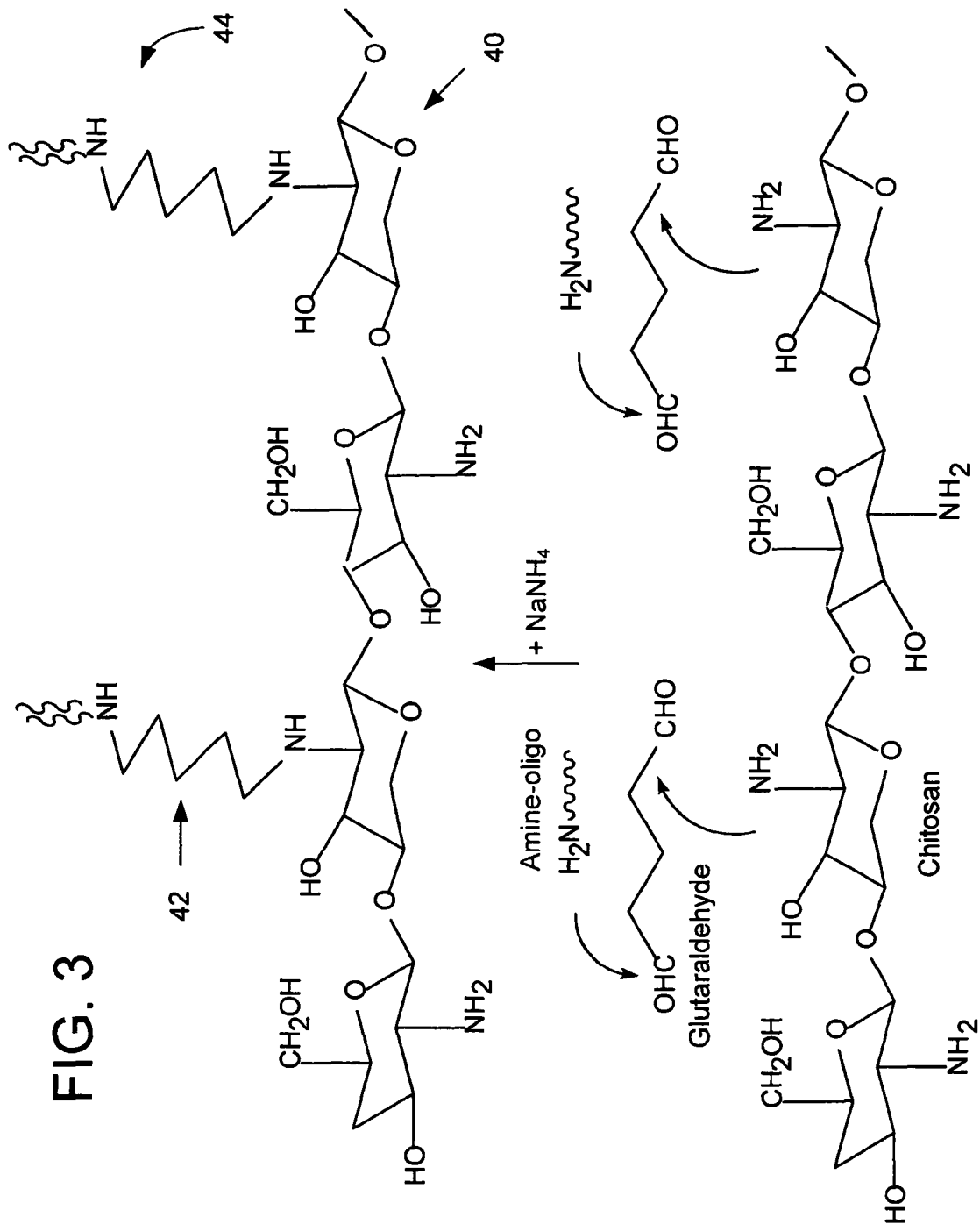
FIG. 3 is a diagram illustrating the chemical structure of chitosan, functionalization with glutaraldehyde as the linking material, and covalent coupling of modified ssDNA as the capture biomolecule.

An exemplary matrix material according to this embodiment would be substantially soluble at a pH below about 4-5, and would be substantially insoluble at a pH above about 6. Exemplary matrix materials include, but are not limited to, chitosan, poly-L-lysine, and combinations thereof. In a preferred embodiment of the biosensor of the present disclosure, chitosan (a primary amine containing biopolymer that is easily extracted from crab shells) serves as a matrix material. The pores in the biopolymer matrix are formed naturally in the deposition by packing similar to a lattice work. Using standard voltammetric techniques the resulting pores can be measured using electrode blocking experiments. Time of and applied potential during deposition effect the biopolymer thickness and pore size thus tuning the electrode blocking. All suitable materials could be processed and examined as described above. FIG. 3 shows the structure of chitosan 40.

As indicated above, the pores/holes are formed in the matrix during the cross-linking or polymerization of the matrix material. With chitosan (or chitin), the size of the holes can be controlled by the degree of polymerization and the thickness of the matrix (i.e., how long the polymerization process is continued and whether additional cross-linking agents are added). The size of the holes is indirectly determined (as opposed to being precisely measured) by determining the change in the redox potential at the electrode. Thus, the slower the rate of reaction, the smaller the holes, because it will take longer for the redox molecules to pass through the matrix and reach the electrode. This is illustrated in Example 1 below, where the more chitosan that is deposited on the electrode (the greater the thickness of the matrix) the more difficult the redox reaction becomes. As further illustrated in Example 2 below, by adding a crosslinking agent (glutaraldehyde) the pores are made even smaller because the crosslinking further constricts the lattice-like framework. As FIG. 2 shows, the peak potential shifted positive in the glutaraldehyde treated electrode, indicating that the redox reaction became more difficult due to the further constriction of the lattice.

In order to make the device a biosensor, a recognition element, or capture biomolecule is placed on the surface of the matrix material. The capture biomolecule is one half of a recognition binding pair. The other half is the target analyte to be detected. The analyte to be detected may be either element of the recognition binding pair (e.g. the receptor or the ligand) or it may be a ligand analog that competes with the ligand for binding to the complement. Suitable recognition binding pairs include, but are not limited to, antigen-antibody, hormone-receptor, drug-receptor, cell surface antigen-lectin, biotin-avidin, and complementary nucleic acid strands. Thus, possibilities for the capture biomolecule, and the target analyte, include, but are not limited to, natural or synthetic nucleotides, proteins, peptides, lipids, and other biomolecules (including synthetic nucleotides and/or peptides with modified backbones such as peptide nucleic acids (PNAs) and Grip-NAs® which form a recognition binding pair). In a preferred embodiment, the capture biomolecule is a capture strand of oligonucleotide and the target analyte is an oligonucleotide where at least a portion of the sequence of the oligonucleotide is complementary to the capture oligonucleotide. FIG. 1 depicts a capture biomolecule 24 as a single stranded polynucleotide that binds a complementary sequence on the target analyte 26.

The amount of capture biomolecule adhered to the matrix should be sufficient so that when the target analyte is bound, the pores of the matrix material are sufficiently blocked to produce a detectable change in the rate of a redox reaction occurring at the electrode. Thus, the size of the capture biomolecule and the target analyte will partially determine the amount of capture biomolecule necessary. Generally, in some preferred embodiments of the biosensor, the packing density of the capture biomolecule is between about $1 \times 10^{11}$ and about $1 \times 10^{13}$ biomolecules/cm$^2$, preferably between about $1 \times 10^{12}$ and about $1 \times 10^{13}$ biomolecules/cm$^2$.

In some embodiments, the capture biomolecule is not directly attached to the matrix material, but is immobilized to the matrix material via a linking material. The linking material may be any molecule capable of immobilizing a capture biomolecule to the matrix material. The linking material may be a homobifunctional linker or a heterobifunctional linker to link various functional groups on the matrix material to the biomolecule of interest. Suitable linking materials include, but are not limited to, glutaraldehyde, homobifunctional imidoesters, and NHS esters. FIG. 3 depicts glutaraldehyde as the linking material 42 attached to a chitosan matrix material 40. The glutaraldehyde then binds the capture biomolecule 44 (here an oligonucleotide) to immobilize it to the matrix material.

In addition, in some embodiments, the transport of the redox molecules in solution is further inhibited by chemically constricting the pores in the chitosan lattice via the addition of a cross-linking material. Thus, some embodiments of the device further include a linking material which serves to further inhibit the flow of the redox species to the electrode and/or to immobilize a capture biomolecule to the matrix material. In one embodiment, glutaraldehyde, a dialdehyde, reacts with the primary amines in a chitosan matrix to form covalent, imine bonds. When added in high concentrations (e.g., single percents by volume) the glutaraldehyde can react at two different primary amines on the chitosan surface creating a crosslinked network that can further restrict the flow of redox molecules to the electrode as described in greater detail in the examples below. Although a linking material, such as glutaraldehyde, can be used to further restrict the pathways through the matrix material, in preferred embodiments of the biosensor, a linking material is used primarily for the immobilization of a capture biomolecule to the matrix material. In such embodiments, the linking material is added only in amounts sufficient to link the desired amount of a capture biomolecule, while not significantly changing the electrochemistry of the system, as illustrated in the examples below.

The biosensor of the present invention also includes a current source, to provide a source of electrons to drive the redox reaction at the electrode, and a signal element, to detect a change in the rate of a redox reaction and the electrode and to report the change. In some embodiments the signal element (e.g., a personal computer (PC)) also records the change in the rate of the redox reaction. In other embodiments the signal element can quantify the amount of target analyte detected based on the degree of shift in the reaction rate. The current source, signal element, and electrode of the biosensor may be set up in a variety of configurations in combination with other standard components of an electrochemical system (such as reference and counter/auxiliary electrodes), that will be known to those of skill in the art. These elements and other aspects of the electrochemical system in which the biosensor operates will be discussed in greater detail below.

Figure 4:
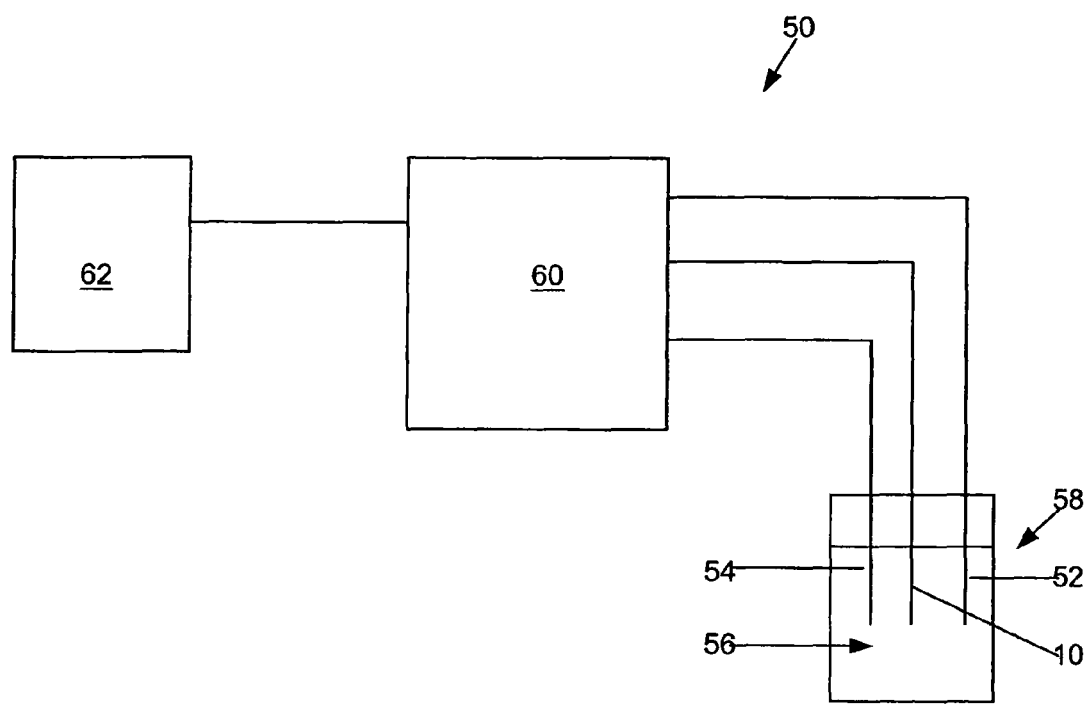
FIG. 4 is a simplified, partly schematic view of an embodiment of the biosensor of the present disclosure.

In one embodiment of the biosensor 50, illustrated in FIG. 4, the working electrode 10 is prepared according to the embodiments described above and immersed in an electrolyte 56 of a buffer solution (e.g., sodium perchlorate, sodium citrate, etc.) containing a redox molecule (e.g., potassium ferricyanide). A counter/auxiliary electrode 52 and a reference electrode 54 are also immersed in the electrolyte to form a three electrode cell 58. The reference and counter electrodes may be made of various conductive materials, just as the working electrode, as discussed above. In some preferred embodiments, the counter electrode is platinum and the reference electrode is Ag/AgCl. The three electrodes are coupled to an electrochemical workstation 60 that provides a current or voltage source to the three electrode cell. This provides a flow of electrons to the three electrode cell to drive a redox reaction that is monitored and measured at the workstation by a signal element 62, which reports and records changes detected in the redox state of the electrodes. The workstation 60 may provide a voltage source to the electrode and measure a current, but it is also capable of working in reverse providing a current source and measuring a voltage. Either set up is acceptable for operating the biosensor of the present disclosure. This figure merely represents one possible embodiment of the biosensor and accompanying electrochemical system according to this disclosure, and other arrangements and embodiments would be known to those of skill in the art and are intended to be covered by the disclosure and claims.

It will also be appreciated by those of skill in the art that the sensing portion of the biosensor of the present disclosure (i.e., the prepared electrode) is reusable. The bound analyte can be removed and the sensor reused to detect the same analyte in a different sample. Alternatively, the capture biomolecule can also be easily removed, and a new capture biomolecule added to use the biosensor for detecting a different analyte. Those of skill in the art will also understand that the biosensor of the present disclosure can be prepared in an array format adapted to detect many different analytes and used for high throughput applications.

Methods of making the biosensor of the present disclosure involve three primary steps: 1) deposit matrix material on the electrode surface, 2) immobilize a capture biomolecule to the surface of the matrix material, and 3) hybridize a target analyte to the capture biomolecule.

Preferably, the matrix material is a polymer and is deposited on the electrode using electrochemical means. Briefly described, the electrode is immersed in a solution including the matrix material, at a pH where the matrix material is soluble, and an electrolyte, to provide the redox species for reacting with the electrode. A counter electrode is also immersed in the solution, and a current is applied across the electrodes to drive a redox reaction. As the reaction occurs and the pH shifts, the matrix material is precipitated onto the surface of the electrode. This process is continued until the desired thickness of matrix material is achieved. Variations of this method would be known to those of skill in the art and are intended to be included herein.

In preferred embodiments, chitosan is the matrix material and deposition of the chitosan on the electrode surface is achieved by using electrochemical deposition. Electrochemical deposition of chitosan (or a similar polymer material) may be achieved by immersing two electrodes (working and counter) in a solution of polymer (e.g. chitosan) and an electrolyte (e.g. potassium ferricyanide), and applying a bias of about 0.5 V to about 2 V across the electrode until the desired thickness of polymer is deposited on the working electrode. The solution is preferably from about 0.01% to about 1% chitosan, most preferably from about 0.5-0.25% chitosan. The electrolyte is preferably from about 0.01 to about 100 mM potassium ferricyanide, most preferably about 0.1 mM potassium ferricyanide. The solution is generally at a relatively acidic or relatively basic pH depending on the solubility of the polymer being deposited; the polymer is desirably soluble in the solution at the starting pH. For chitosan, the solution is preferably at a generally acidic pH, most preferably at a pH of about 2.5. In preferred embodiments, a bias of about 2 V, preferably with no more than about a 2 mA current limit, is applied across the electrodes to achieve precipitation of the polymer onto the working electrode. As the potential is swept positive the current starts to flow as the potassium ferricyanide is oxidized. This happens very easily (low potential) at the bare electrode and becomes increasingly more difficult (peak shifts positive) as more chitosan is deposited onto the surface. The bias is held until the desired thickness of matrix material is achieved.

Figure 5:
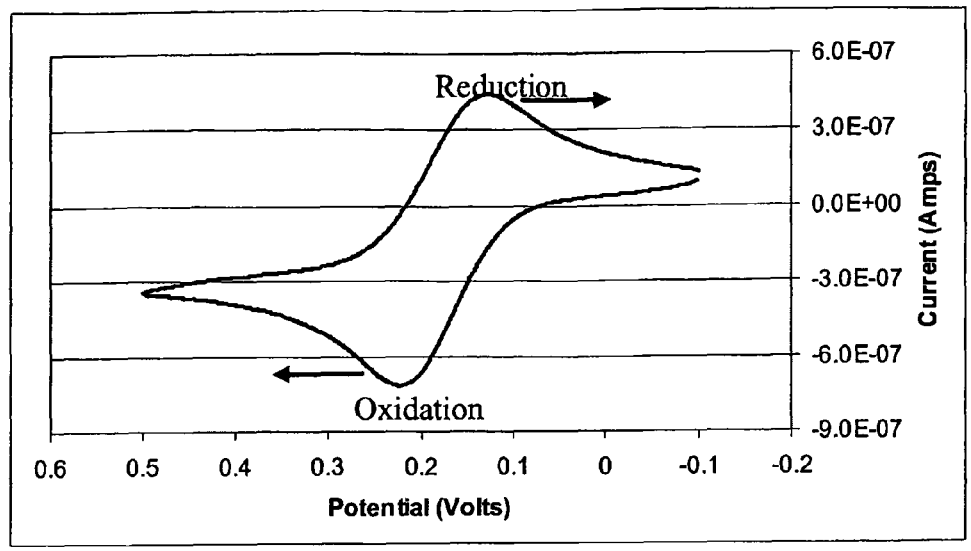
FIG. 5 is a schematic of a cyclic voltammogram showing the direction of peak shifts upon binding of a target analyte to the biosensor of the present disclosure.
Figure 6:
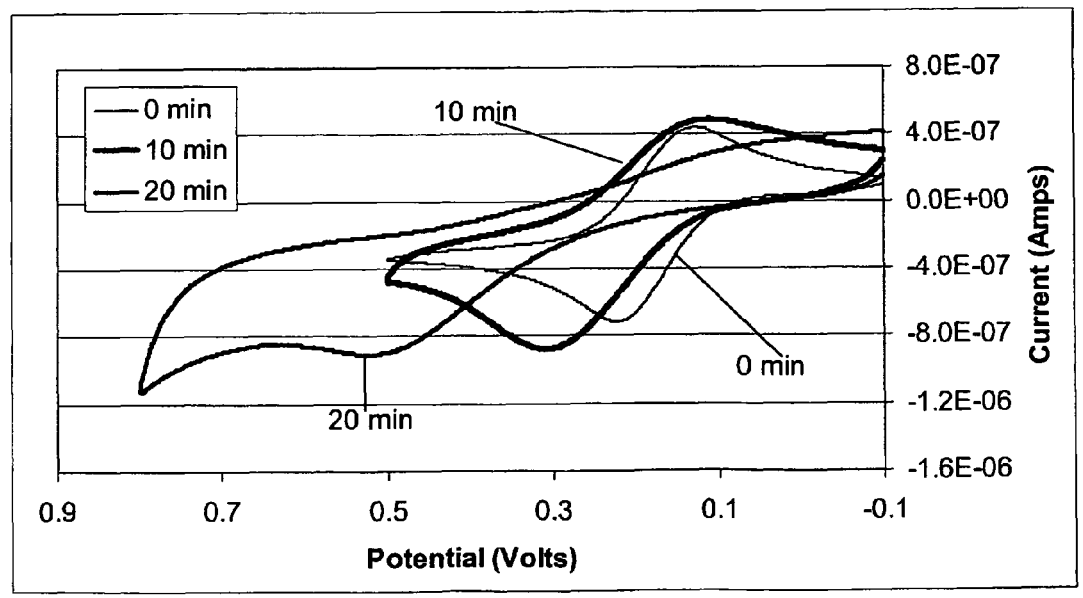
FIG. 6 shows cyclic voltammograms of redox potential as a function of the thickness of the matrix material (chitosan).

FIG. 5 is an illustration of a cyclic voltammogram showing the oxidation peak and reduction peak and the direction of shift that will occur as the potential changes at the electrode. FIG. 6 is a cyclic voltammogram illustrating the change in the redox potential after 10 and 20 minutes of chitosan deposition. This is a clear demonstration that the flow of redox molecules to the electrode surface is not stopped, but is dramatically hindered by the chitosan lattice.

Next, the capture biomolecule is immobilized on the matrix material to convert the system into a biosensor. Preferably, the capture biomolecule is added without significantly altering the electrochemistry of the system, so that the primary shift in electrochemistry occurs after the binding of the target analyte. The capture biomolecule can be immobilized to the matrix material directly or via the use of a linking material, depending on the type of matrix material used and the nature of the capture biomolecule and the respective functional groups. Those of skill in the art will know a variety of methods for immobilizing a capture biomolecule to the matrix material, depending on the functional groups involved. In a preferred embodiment of the disclosure, as illustrated in FIG. 3, this can be accomplished using chitosan as the matrix material, glutaraldehyde as a linking material, and an oligonucleotide as the capture biomolecule. In other embodiments a capture oligonucleotide strand can also be immobilized directly to the chitosan matrix without the use of a linking material. The desired packing density of the capture biomolecule will, in part, determine the concentrations of capture biomolecule and linking material to be used in immobilizing the capture biomolecule to the matrix material.

After immobilization of the capture biomolecule, the thus prepared electrode is incorporated into an electrochemical system including a current source for providing a flow of electrons to drive a redox reaction at the electrode and a signal element for detecting and reporting a change in the rate of the reaction. The system also preferably includes a reference and counter/auxiliary electrode, and various other standard elements of an electrochemical system as depicted in an embodiment illustrated in FIG. 4 and briefly described above. Preferably, the signal element is also capable of recording changes in the rate of a redox reaction and calculating the amount of bound analyte based on the detected shift. This is accomplished using various standard electrochemical techniques known to those of skill in the art, some of which are discussed in greater detail below.

Embodiments of this disclosure also include methods of using the biosensor of this disclosure to detect a target analyte in a sample to be analyzed. A biosensor is made according to the methods described above with a working electrode having a matrix coating and a capture biomolecule attached thereto. The capture biomolecule selected is one half of a recognition binding pair with the analyte to be detected. The electrode is then immersed in a sample to be analyzed (e.g., in sufficient contact with the sample for a target analyte contained in the sample to bind to the capture biomolecule) and the system is interrogated using standard electrochemical techniques. As discussed above, the biosensor also preferably includes a current source to provide a flow of electrons to drive a redox reaction at the electrode and a signal element for detecting and reporting a change in a rate of the reaction.

Various electrochemical techniques can be employed in such a system including, but not limited to, various forms of voltammetry, impedance and amperometry, such as cyclic voltammetry, AC voltammetry, AC impedance, square wave voltammetry and differential pulse voltammerty. Most of the above techniques may all be applied with the same electrochemical set up, but with different characteristics to the applied and measured voltages and currents. Any differences to the electrochemical set up that would be required to implement a different electrochemical technique would be understood by those of skill in the art and are intended to be included in the scope of the disclosure.

After hybridization of the target analyte to the capture biomolecule on the biosensor, the signal change is measurable by electrochemical signaling. Basically, before hybridization an electrochemical signal is generated, and after hybridization transport of the redox species, and thus the signal generation, is blocked (or substantially reduced) at a given electrode potential. In some of the examples detailed below the target analyte tested was a sequence of complementary, synthetic oligonucleotide, and thus the signal shift, though detectable and highly reproducible, was relatively small. In actual samples encountered following a cell rupture technique the genetic sequence would likely be quite long (e.g., on the order of thousands of DNA base pairs). Therefore, when hybridization with the complementary sequence immobilized on the chitosan occurs, the relatively large target analyte blocks a large percentage of the pathways leading to the electrode surface. This significantly affects the ability for charged species from the solution to reach the electrode and dramatically changes the impedance (increase) and the voltammetric signal (decrease the peak height and shift the redox potential positive). The effect is linear, depending on the quantity of oligonucleotide captured at the chitosan interface, thereby also enabling quantification of the amount of target analyte detected.

Having generally described electrochemical biosensors according to the present disclosure and methods of making and using such biosensors, the examples that follow describe some specific embodiments. While embodiments of the biosensor and methods of making and using the biosensor are described in connection with the following examples and the corresponding text, there is no intent to limit embodiments to these examples. On the contrary, the intent is to cover all alternatives, modifications, and equivalents included within the scope of the disclosure.

EXAMPLES

Example 1

This example describes the deposition of chitosan, as the matrix material, on an electrode and demonstrates the effect on the electrode potential. Electrochemical deposition of chitosan was performed on gold electrodes, and the ability for the chitosan layer to block the oxidation of a redox molecule (potassium ferricyanide) was characterized.

Two electrodes were immersed in a solution (0.5-0.25%) of chitosan at pH 2.5. A bias of 2 V was applied across the electrodes and held for various amounts of time. As the potential is swept positive, the current starts to flow as the potassium ferricyanide is oxidized. FIG. 6 is a cyclic voltammogram (CV) of gold electrodes before, after 10 minutes and after 20 minutes of deposition, with potassium ferricyanide (0.1 mM) on chitosan (0.5%) coated (2 V) electrodes (Peak Potentials: 0 Min=223 mV; 10 Min=309 mV; 20 Min=522 mV). FIG. 6 illustrates that the redox reaction happens very easily (low potential) at first and becomes much more difficult (peak shifts positive) as more chitosan is deposited onto the surface. This is a clear demonstration that the flow of redox molecules to the electrode surface is dramatically slowed by the chitosan lattice, and that the rate of the reaction is directly related to the thickness of the chitosan deposit.

Example 2

Figure 7:
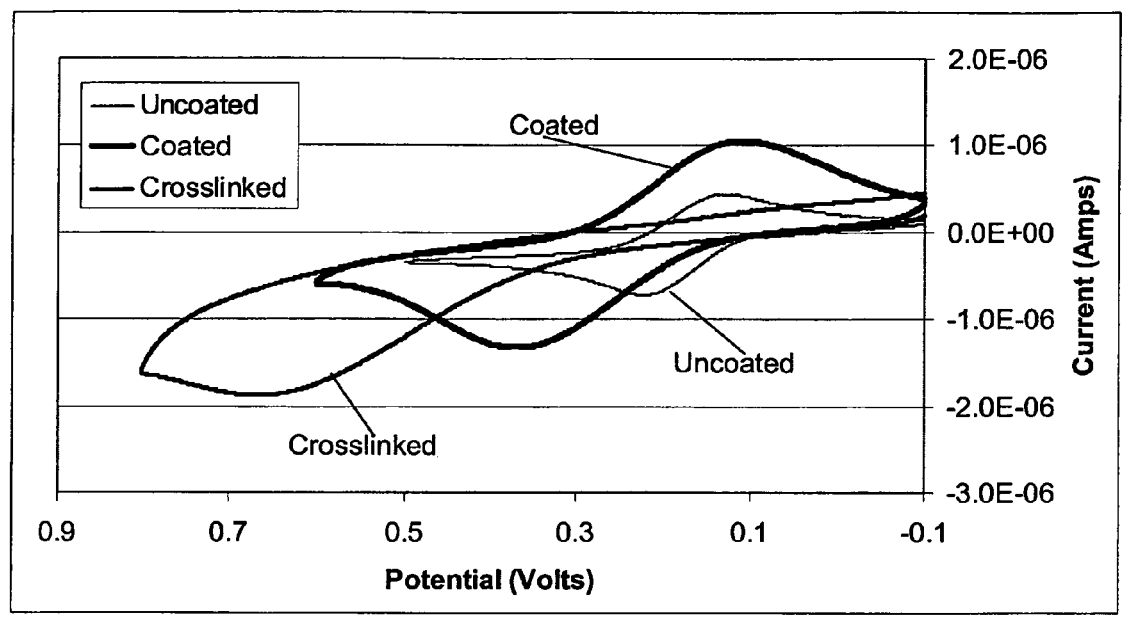
FIG. 7 shows cyclic voltammograms of redox potential as a function of coating with matrix material and crosslinking with 4% glutaraldehyde.

This example demonstrates that the blocking ability of the matrix material may also be affected by chemically constricting the pores in the chitosan lattice as opposed to just increasing the thickness of the matrix material. In this example, cross-linking of the chitosan through glutaraldehyde treatment further inhibits the flow of redox molecules in solution to the electrode. Concentrations of 4.0% glutaraldehyde were used in this example to demonstrate the extensive closing of the pores in the chitosan lattice. The chitosan-coated electrodes were first exposed to 4.0% v/v glutaraldehyde aqueous solutions then rinsed in deionized water to remove unreacted glutaraldehyde, and CVs were run to test the system. FIG. 7 is a CV, with potassium ferricyanide (0.1 mM) as the electrolyte, of an uncoated, chitosan coated and coated/glytaraldyhde crosslinked electrode (4% glutaraldehyde) (Peak Potentials: Uncoated=223 mV; Coated=366 mV; Cross-linked=667 mV).

Glutaraldehyde, a dialdehyde, reacts with the primary amines in chitosan to form covalent, imine bonds. When added in higher concentrations, as in this example, the glutaraldehyde can react at two different primary amines on the chitosan surface. This causes substantial crosslinkig, which further restricts redox molecule flow to the electrode surface, as confirmed by hundreds of millivolt shifts in the oxidation peak, as shown in FIG. 7. This illustrates that it is possible to chemically influence the size of the pathways in the chitosan and to electrochemically measure these changes, demonstrating the sensor capabilities.

Example 3

Figure 8:
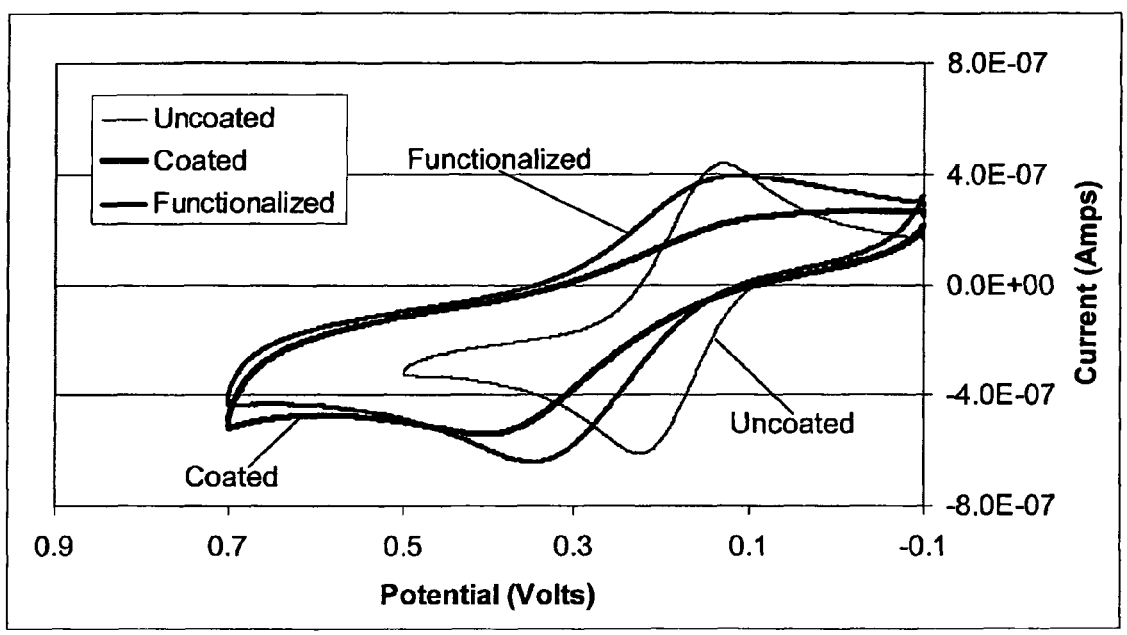
FIG. 8 shows cyclic voltammograms of redox potential as a function of functionalization with 0.1% glutaraldehyde.

This example illustrates that the linking material and capture biomolecule can be added without significantly altering the electrochemistry of the system so that further change is not apparent after hybridization. This was accomplished using the glutaraldehyde as a linking material, as discussed in Example 2, but in lower concentrations. FIG. 8 shows CVs of potassium ferricyanide (0.1 mM) before and after functionalization of the chitosan with 0.1% glutaraldehyde (Peak Potentials: Uncoated=224 mV; Coated=402 mV; Functionalized=352 mV). Note that the oxidation peak actually shifted negative after the reaction with the glutaraldehyde. This indicates that the use of low concentrations of glutaraldehyde should not have a deleterious effect on the electrochemistry, and it was determined by additional experiments that 0.05% glutaraldehyde is sufficient for oligonucleotide immobilization.

Example 4

This example describes the addition of the capture biomolecule. This was achieved by immobilizing a relatively small (20-30 DNA bases long) capture molecule to the chitosan matrix material. In order to immobilize the oligonucleotides, the chitosan-coated and 0.05% glutaraldehyde-treated electrodes were soaked in 2 µg/mL of amine terminated oligonucleotide. This solution was prepared in 6× saturated sodium citrate (6×SSC) buffer and allowed to react overnight at 4 C, after which any remaining unbound oligonucleotide was washed away.

Example 5

This example describes one embodiment of the biosensor of the current disclosure. Chitosan-coated electrodes were prepared by dissolving appropriate quantities of chitosan flakes in dilute HCl. Films were electrodeposited by placing a 2 V bias between a gold working electrode and a platinum counter electrode while immersed in 0.25% w/v chitosan solution at pH 2.5. Deposition times were varied from 1 minute to 30 minutes. The films were then neutralized by soaking in 1M NaOH. The excess base and salt formed were then removed by soaking in deionized water. Coated electrodes were stored in deionized water.

The primary amine groups on the chitosan film were then modified using glutaraldehyde. The chitosan-coated electrodes were exposed to concentrations of 0.05%-4.0% v/v glutaraldehyde aqueous solutions. The electrodes were then rinsed in deionized water to remove unreacted glutaraldehyde. It was found that concentrations of 0.05% were adequate for the immobilization of amine-terminated oligonucleotides for hybridization experiments while having no significant effect on the electrochemistry of the chitosan coated electrodes.

The last step was to actually perform oligonucletide-oligonucleotide hybridization on the modified chitosan surface. DNA oligonucleotide sequence of the *E. coli* gene dnaK (5'-NH2-CTT TCG CGT TGT TTG CAG AA), SEQ ID NO: 1, with its complementary target sequence (5'-TTC TGC AAA CAA CGC GAA AG), SEQ ID NO: 2, was utilized. This 20-mer target sequence is located near the 3' end of the dnaK gene and was selected because the specific region had little homology to other *E. coli* genomic sequences.

In order to immobilize oligonucleotides the chitosan-coated and 0.05% glutaraldehyde-treated electrodes were soaked in 2 µg/mL of amine terminated oligonucleotide. This solution was prepared in 6× saturated sodium citrate (6×SSC) buffer and allowed to react overnight at 4° C.

A target strand that was a matched-length, perfect complement to the capture strand was reacted in the refrigerator for two hours to complete the hybridization. Hybridizations were preformed using 10 nanomolar complement in 6×SSC buffer. The reaction was allowed to take place for 2 hours at 4° C. but could be much more rapid at room or elevated temperatures. The electrodes were extensively washed with buffer at room temperature to remove any unbound oligonucleotides.

All electrochemistry was performed on a CH Instruments 660a electrochemical workstation. The electrodes were 2.0 mm gold disk working, platinum wire counter and Ag/AgCl reference. Cyclic voltammograms (CVs) at a sweep rate of 10 mV/sec were taken at every step of electrode modification as well as before and after hybridization. The electrolyte was 6×SSC with 0.1 mM potassium ferricyanide as the redox molecule.

Figure 9A:
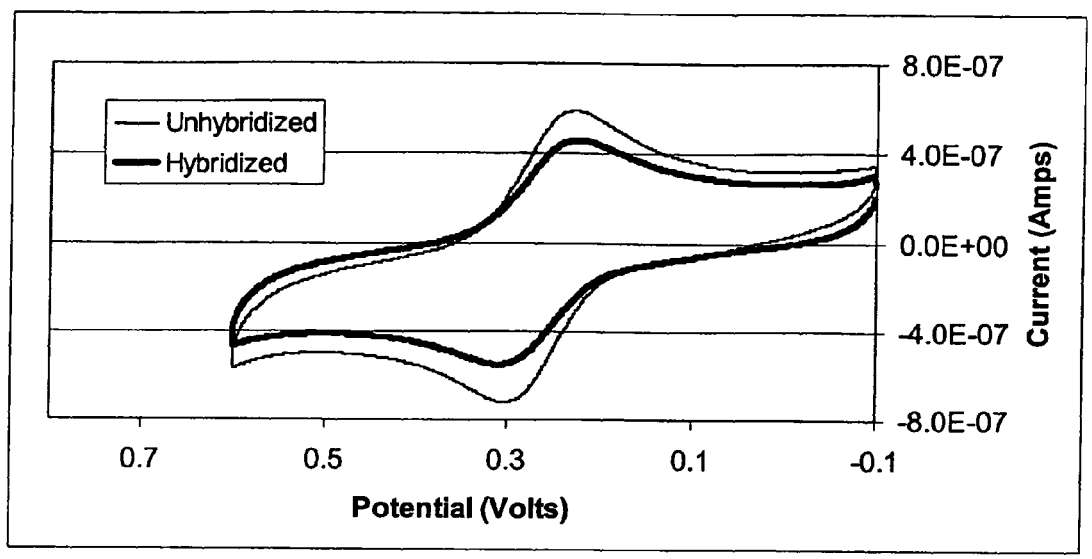
FIG. 9A is a cyclic voltammogram of potassium ferricyanide (0.1 mM) and effect of hybridization of a target analyte.
Figure 9B:
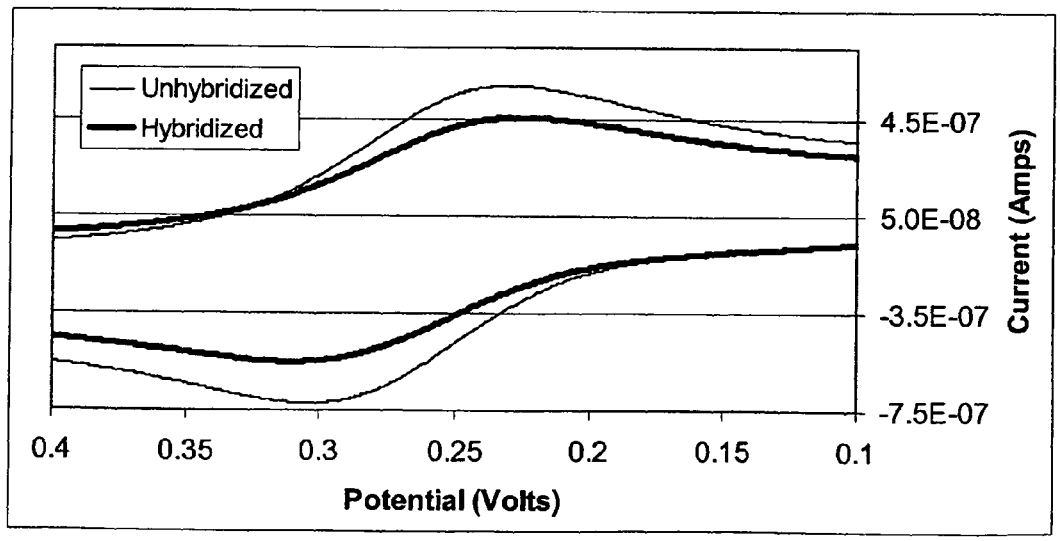
FIG. 9B is a magnification of the peak shifts between the cyclic voltammograms of FIG. 9A.

The results of two CVs are shown in FIG. 9, showing a 9 mV shift in peak splitting. Although the hybridization did not give a dramatic shift on either the oxidation or reduction peak, the shift was reproducible in triplicate. It is probably best described by peak splitting or the difference in voltage between the location of the maximum oxidation and reduction currents. The difference in peak splitting was consistently 9 mV, which is not extremely large but is easily measurable on the electrochemical workstation used. These results show relatively small but highly reproducible potential shifts. If a larger oligonucleotide, genomic DNA or fragments were used as the target this splitting should become much more dramatic. Thus, in most practical applications, the sensor of the present disclosure will actually show more dramatic signal changes due to the larger size of the target analyte.

It should be emphasized that the above-described embodiments are merely possible examples of implementations. Many variations and modifications may be made to the above-described embodiments. All such modifications and variations are intended to be included herein within the scope of this disclosure and protected by the following claims.

REFERENCES

Each of the references cited in this disclosure is incorporated by reference in its entirety.

1) DeLisa, M. P.; Wu, C. F.; Wang, L.; Valdes, J. J.; Bentley, W. E. *J. Bacteriol.* 2001, 18, 5239-5247.
2) Shalon, D.; Smith S. J.; Brown, P. O. *Genome Res.* 1996, 7, 639-645.
3) Sumner, J. J.; Creager, S. E. *J. Phys. Chem. B,* 2001, 105, 8739-8745.
4) Yu, C. J.; Wan, Y. J; Yowanto, H.; Li, J.; Tao, C. L.; James, M. D.; Tan, C. L.; Blackburn, G. F.; Meade, T. J. *J. Am. Chem. Soc.* 2001, 123, 11155-11161.
5) Wang, J.; Liu, G. D.; Merkoci, A. *Anal. Chim. Acta* 2003, 482, 149-155.
6) Wang, J.; Kawde, A. N.; Musameh, M. *Analyst* 2003, 128, 912-916.
7) Armistead, P. M.; Thorp, H. H. *Anal. Chem.* 2000, 72, 3764-3770.
8) Fernandes, R.; Wu, L. Q.; Chen, T.; Yi, H.; Rubloff, G. W.; Ghodssi, R.; Bentley, W. E.; Payne, G. F. *Langmuir* 2003, 19, 4058-4062.
9) Wu, L. Q.; Gadre, A. P.; Yi, H.; Kastantin, M. J.; Rubloff, G. W.; Bentley, W. E.; Payne, G. F.; Ghodssi, R. *Langmuir* 2002, 18, 8620-8625.
10) Yi, H.; Wu, L. Q.; Sumner, J. J.; Gillespie, J. B.; Payne, G. F.; Bentley, W. E. *Biotechnology and Bioengineering* 2003, 83, 646-652.

I claim:
1. A biosensor comprising:
a) an electrode;
b) a non-conductive polymer deposited on the electrode to form a matrix material having a plurality of pores therethrough;
c) a capture biomolecule immobilized on the matrix material capable of binding a target analyte in a sample to be analyzed; wherein the binding of the target analyte to the capture biomolecule effectively blocks a sufficient number of pores in the matrix material to produce a measurable decrease in the rate of a redox reaction occurring at the electrode;
d) a current source, wherein the current source provides a flow of electrons to drive a redox reaction at the electrode between the electrode and a redox species in contact with the electrode; and
e) a detector element coupled to the electrode to detect the measureable decrease a change in the rate of a redox reaction occurring at the electrode due to the number of pores in the matrix material blocked by the binding of the target analyte.

2. The biosensor of claim 1, wherein the matrix material comprises chitosan and the electrochemical deposition of chitosan is performed on the electrode, and wherein the capture biomolecule is unlabeled, and wherein the pores of the matrix material are large enough to permit a flow of a redox species to the electrode, and wherein the pores are small enough to substantially prevent the flow of any contaminating molecules present in the sample to be analyzed to the electrode.

3. The biosensor of claim 1, wherein the binding of the target analyte to the capture biomolecule results in the target analyte blocking a significant percentage of the pores leading to the electrode resulting in an increase in the impedance.

4. The biosensor of claim 1, wherein electrode is immersed in an electrolyte comprising redox molecules and wherein the binding of the target analyte to the capture biomolecule significantly affects the ability for the redox molecules to reach the electrode, thereby decreasing the rate of redox detected by the detector element.

5. The biosensor of claim 1, wherein the capture biomolecule is a nucleic acid sequence.

SEQUENCE LISTING

<160> NUMBER OF SEQ ID NOS: 2

<210> SEQ ID NO 1
<211> LENGTH: 20
<212> TYPE: DNA
<213> ORGANISM: E. coli dnaK

<400> SEQUENCE: 1
ctttcgcgtt gtttgcagaa                                            20

<210> SEQ ID NO 2
<211> LENGTH: 20
<212> TYPE: DNA
<213> ORGANISM: E. coli dnaK

<400> SEQUENCE: 2
ttctgcaaac aacgcgaaag                                            20

6. The biosensor of claim 1, wherein the capture biomolecule is a protein or peptide.

7. The biosensor of claim 1, wherein the signal element further quantifies the amount of target analyte present in the sample based on the amount of change in the rate of the redox reaction occurring at the electrode.

8. The biosensor of claim 1, wherein the packing density of the capture biomolecule on the matrix is in a range of about $1\times10^{11}$ to about $1\times10^{13}$ per square centimeters.

9. The biosensor of claim 1, wherein the redox species is contained in an aqueous solution in contact with the electrode.

10. The biosensor of claim 9, wherein the redox species is potassium ferricyanide.

11. The biosensor of claim 1, wherein the nonconductive polymer comprises a chitosan film that is electrochemically deposited on electrode surface, and the capture biomolecule comprises an unlabeled immobilized capture strand of oligonucleotide which is immobilized to the surface of the chitosan film.

12. The biosensor of claim 11, further comprising glutaraldehyde having a concentration in the range of 0.05 to approximately 0.1% so that there are enough bonding sites for the capture biomolecule in order to obtain sufficient packing density to yield the blocking effect, yet not significantly in excess of 0.1% glutaraldehyde so that cross-linking of the matrix material and closing of the pores occurs, and potassium ferricyanide; and wherein the concentration of chitosan is within the range of about 0.01% to 1%.

13. The biosensor of claim 1, wherein the capture biomolecule is a first element of a binding pair and the target analyte is a second element of the binding pair; and wherein neither the capture biomolecule nor the target analyte interacts with the redox molecules to generate redox products.

14. The biosensor of claim 13, wherein the binding pair is selected from: antigen-antibody, hormone-receptor, drug-receptor, cell surface antigen-lectin, biotin-avidin and complementary nucleic acid sequences.

15. The biosensor of claim 13, wherein the binding pair comprises complementary nucleic acid sequences and wherein the nucleic acid sequence of the capture biomolecule is complementary to at least a portion of the sequence of a target analyte.

16. The biosensor of claim 1, wherein the matrix material is a non-conductive polymer having a functional group capable of binding a capture biomolecule or a linking material and wherein the matrix material is deposited on the electrode by electrochemical deposition to thereby form a lattice; and wherein the pores in the lattice are chemically constricted by a cross-linking material.

17. The biosensor of claim 16, wherein the non-conductive polymer is substantially soluble at a generally acidic pH or a generally basic pH and is substantially insoluble at a generally neutral pH.

18. The biosensor of claim 17, wherein the non-conductive polymer is selected from: chitosan, poly-L-lysine, and combinations thereof.

19. A biosensor comprising:
a) an electrode;
b) a matrix material deposited on the electrode, wherein the matrix material comprises a plurality of pores therethrough;
c) a capture biomolecule immobilized on the electrode capable of binding a target analyte in a sample to be analyzed, wherein the binding of the target analyte to the capture biomolecule effectively blocks a sufficient number of pores in the matrix material to produce a measurable decrease in the rate of a redox reaction occurring at the electrode; and
d) a detector element coupled to the electrode to detect the measureable decrease in the rate of a redox reaction occurring at the electrode in order to detect the presence of the target analyte due to the number of pores in the matrix material blocked by the target analyte.

20. A method of making a biosensor comprising:
a) providing an electrode;
b) immersing the electrode in a solution of a non-conductive polymer material;
c) running a current to the electrode sufficient to cause the non-conductive polymer material to deposit on the surface of the electrode, thereby forming a matrix material having a plurality of pores therethrough;
d) immobilizing an unlabelled capture biomolecule capable of binding a target analyte onto the matrix material, wherein the binding of the target analyte by the capture biomolecule effectively blocks a sufficient number of pores in the matrix material to produce a measurable decrease in the rate of a redox reaction occurring at the electrode; and
e) coupling the electrode to a signal element to detect and report a change in the rate of a redox reaction occurring at the electrode.

21. A method of detecting a target analyte in a sample to be analyzed comprising:
a) immersing an electrode in the sample to be analyzed, wherein the electrode comprises:
i) a non-conductive polymer deposited on the electrode to form a matrix material having a plurality of pores therethrough, and wherein the matrix material is of sufficient thickness to produce a detectable change in the rate of a redox reaction occurring at the electrode; and
ii) an unlabelled capture biomolecule immobilized on the electrode capable of binding the target analyte contained in the sample to be analyzed, wherein the binding of the target analyte to the capture biomolecule effectively blocks a sufficient number of pores in the matrix material to produce a measurable decrease in the rate of a redox reaction occurring at the electrode,
b) providing a flow of electrons to drive a redox reaction at the electrode between the electrode and a redox species in contact with the electrode; and
c) detecting and reporting a change in the rate of a redox reaction occurring at the electrode that signals the binding of the target analyte to the capture biomolecule.

* * * * *